United States Patent [19]

Kapadia

[11] Patent Number: 5,684,035

[45] Date of Patent: Nov. 4, 1997

[54] ANTIMALARIAL AGENTS

[76] Inventor: Govind J. Kapadia, 9636 Red Coat La., Potomac, Md. 20854

[21] Appl. No.: 682,297

[22] Filed: Jul. 17, 1996

[51] Int. Cl.$^6$ .......................... A61K 31/12; A61K 31/19; A61K 31/40; A61K 31/135

[52] U.S. Cl. .......................... 514/429; 514/553; 514/577; 514/657; 514/682

[58] Field of Search ........................ 514/429, 657, 514/682, 577, 553

[56] References Cited

U.S. PATENT DOCUMENTS

| | | | |
|---|---|---|---|
| 2,396,665 | 3/1946 | Ladd | 514/682 |
| 2,553,648 | 5/1951 | Feiser | 260/396 |
| 2,554,648 | 5/1951 | Stickley | 315/257 |
| 2,829,082 | 4/1958 | O'Brien | 167/32 |
| 3,624,066 | 11/1971 | Feiser | 260/197 |
| 4,225,619 | 9/1980 | Brickl | 424/331 |
| 5,053,418 | 10/1991 | Latter et al. | 514/682 |
| 5,053,432 | 10/1991 | Hudson et al. | 514/682 |
| 5,175,319 | 12/1992 | Hudson | 552/297 |

FOREIGN PATENT DOCUMENTS

| | | |
|---|---|---|
| 77551 | 4/1983 | European Pat. Off. . |
| 2159056 | 11/1985 | United Kingdom . |

OTHER PUBLICATIONS

Feiser, J. Amer. Chem. Soc., vol. 70, pp. 3156–3174 (1948).

*Primary Examiner*—Allen J. Robinson
*Attorney, Agent, or Firm*—Papan Devnani, Esq.; Thomas A. Powers; Chandrakant C. Shroff

[57] ABSTRACT

The invention is directed to a method of killing or inhibiting the growth of the malaria-causing pathogen *Plasmodium falciparum* by exposing the pathogen to an effective amount of a preparation comprising a compound selected from the group consisting of:

a) a compound of formula I:

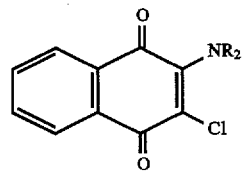

where $-NR_2$ is $-NH_2$ or $-N(CH_2)_3CH_2$;

b) a compound of formula II;

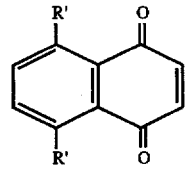

where each R' is —H or each R' is —OH; and c) a compound of formula III;

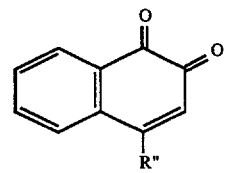

where R" is —NH$_2$, —H, or —SO$_3$M, and where M is H, Na, or K.

10 Claims, 2 Drawing Sheets

ANTIMALARIAL AGENTS

The present invention relates to therapeutic uses of naphthoquinones and/or aspidinol derivatives. More particularly, it relates to their use as antimalarial agents.

BACKGROUND OF THE INVENTION

Malaria, a disease caused by the human parasite *Plasmodium falciparum*, is a serious problem, particularly in tropical and Third World countries. The disease is typically transmitted to humans by the bite of infected mosquitoes. Fortunately, drugs which are able to cure malaria by killing *P. falciparum* are known. These drugs include chloroquine, mefloquine, pyrimethamine, and sulfadoxine.

However, a new problem has emerged with the appearance of new strains of *P. falciparum* which are resistant to known antimalarial drugs. Two such drug-resistant *P. falciparum* strains are the Indochina III/CDC, or $W_2$, strain and the Sierra Leone I/CDC, or $D_6$, strain. The $W_2$ strain is resistant to chloroquine, pyrimethamine, and sulfadoxine, but susceptible to mefloquine. The $D_6$ strain is resistant only to mefloquine. Other drug-resistant strains of malaria are currently known, and more are likely to appear in the future. Therefore, it is necessary to design and develop new and different antimalarial drugs that are effective against normal and drug-resistant strains.

Compounds which have been found to be particularly effective against malaria-causing parasites include 2-alkyl-3-hydroxy-naphthoquinones and 2-cycloalkyl-3-hydroxynaphthoquinones, as reported by Fieser et al. (U.S. Pat. No. 2,553,648 and other publications) and, more recently, by Hudson et al. (European Patent Application 77,551 and U.S. Pat. No. 5,053,432). While some of these have shown promise as antimalarial drugs, others have been found to require overly large doses to achieve the desired effect in man. Additionally, these compounds often show other pharmacological properties which limit their selectivity.

Our approach to the discovery of new classes of antimalarial compounds is to investigate compounds which are known to have anti-infective activity against microorganisms. We hope to uncover evidence of antimalarial activity against *P. falciparum* by these compounds. Quinones are known to be anti-infective agents. For example, polyhydroxy-1,4-naphthoquinones are effective against several species of bacteria and fungi, as shown by Sime (U.K. Patent Application 2,159,056). 2-Amino-3-chloro-1,4-naphthoquinone is also known to have biocidal activity against fungi, as shown by O'Brien (U.S. Pat. No. 2,829,08). However, these compounds were not investigated for antimalarial activity against *P. falciparum*. Resorcinol derivatives such as methylene-bis-(2,6-dihydroxy-3-trifluoroacetyl-5-alkylbenzenes and methylene-bis-(2,4-dihydroxy-3-trifluoroacetyl-5-alkylbenzenes have also been shown to have antibacterial activity (Brickl et al., U.S. Pat. No. 4,225,619). Again, it is unknown whether any of these compounds are effective against *P. falciparum*. We, therefore, investigated the compounds described above or structurally similar compounds with the hope that the bioactivity of these compounds extended to malaria-causing parasites.

It is an object of this invention to find new ways of combatting malaria by identifying additional compounds that will inhibit the growth of or kill the *P. falciparum* parasite.

It is a further object to combat malaria by finding compounds that will inhibit the growth of or kill drug-resistant strains of *P. falciparum*.

SUMMARY OF THE INVENTION

It has now been found that certain substituted naphthoquinones as described below exhibit high activity against *P. falciparum*. Certain of these compounds exhibit activity which is comparable to that of sulfadoxine.

The invention, in a first aspect, provides a method of inhibiting the growth of *P. falciparum* by exposing the organism to a preparation of any of various naphthoquinones. These may include compounds of formula I:

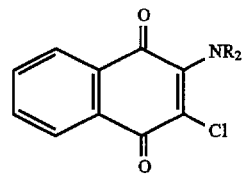

where —$NR_2$ may be either —$NH_2$ or a pyrrolidine ring;

compounds of formula II:

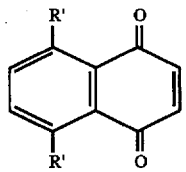

where each —R' is —H or each —R' is —OM, where M is a metal cation, preferably an alkali metal or ammonium cation; or compounds of formula III:

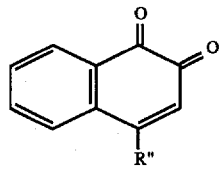

where R" is —$NH_2$, —H, or —$SO_3M$. Compounds of formula I have been found to be of particular interest as antimalarially active naphthoquinone derivatives. 2-amino-3-chloro-1,4-naphthoquinone is particularly preferred.

In a second aspect, certain aspidinol derivatives have also been found to be effective in combatting *P. falciparum*. The most effective compounds of this type are those of formula IV:

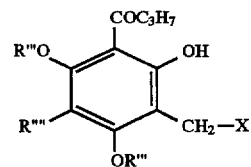

where each R'" is —H or —$CH_3$, R"" is —H or —$CH_3$, and —X is either:

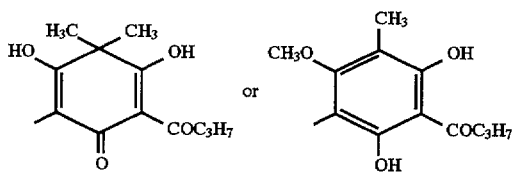

with the further proviso that the two R'" groups are different from each other. This result is somewhat unexpected, as compounds of this type are primarily known as anthelmintics or as antidiarrhoeics.

DETAILED DESCRIPTION OF THE INVENTION

I. Naphthoquinones

Figure 1:
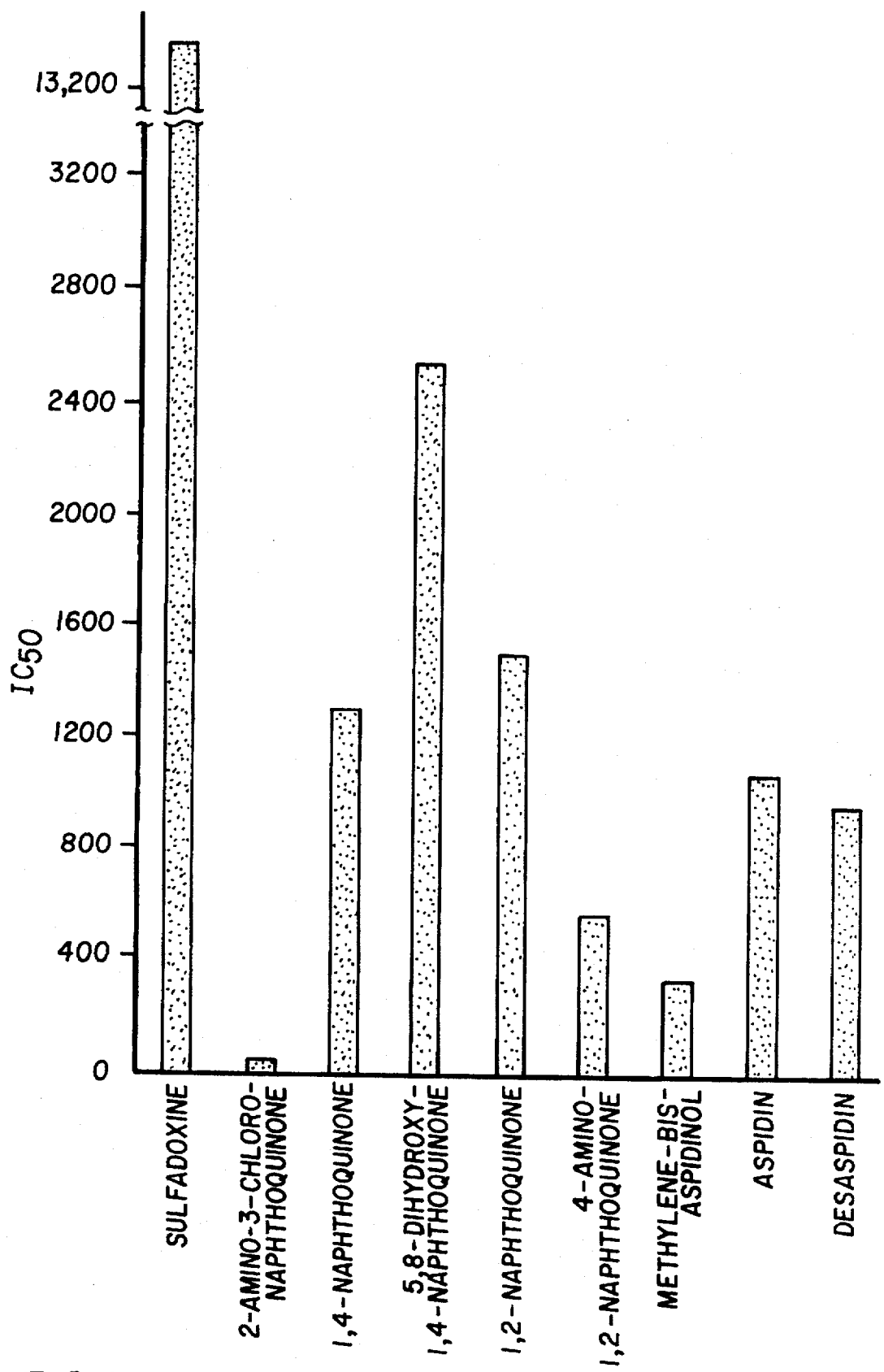
FIG. 1 compares the antiplasmodial activity of selected naphthoquinones and aspidinol derivatives toward the $W_2$ strain of *P. falciparum* to that of sulfadoxine.

A series of naphthoquinone derivatives were tested as antimalarial agents by a serial dilution technique. A solution of each compound in a RPMI-1640 culture medium was prepared at a starting concentration of 50,000 ng/mL. An RPMI-1640 culture of *P. falciparum* containing 10% normal plasma was prepared using standard cell culture techniques. The plasma provides trace amounts of folic acid and p-aminobenzoic acid, and serves to promote rapid growth of the microorganism. The culture was then exposed to the preparation of the antimalarial candidate compound. If the compound appeared to inhibit the growth of the microorganism, the preparation was then diluted by a defined amount, and the experiment was repeated. This is continued until the concentration at which 50% of the organisms are killed ($IC_{50}$) and the concentration at which 90% of the organisms are killed ($IC_{90}$) are determined. Each compound was tested against both the $W_2$ and the $D_6$ strains of *P. falciparum*.

Several substituted 2-amino-3-chloro-1,4-naphthoquinones were tested, and the results are listed in Table 1. The most effective of these compounds was found to be 2-amino-3-chloro-1,4-naphthoquinone. The activity of this compound against $W_2$ *P. falciparum* is compared to that of sulfadoxine in FIG. 1. The $IC_{50}$ against the chloroquine-, pyrimethamine-, and sulfadoxine-resistant $W_2$ strain of *P. falciparum* was 37.3 ng/mL, and the $IC_{90}$ against this strain was 83.4 ng/mL. The $IC_{50}$ value of 2-amino-3-chloro-1,4-naphthoquinone against the $W_2$ strain is considerably lower than that of chloroquine, pyrimethamine or sulfadoxine, indicating that 2-amino-3-chloro-1,4-naphthoquinone has the potential to be a useful addition to the medical practitioner's arsenal of drugs effective against drug-resistant strains of *P. falciparum*. As shown in Table 1 and FIG. 2, this compound was also found to be effective against the mefloquine-resistant $D_6$ strain of *P. falciparum*, with an $IC_{50}$ of 192.0 ng/mL and an $IC_{90}$ of 355.9 ng/mL.

TABLE 1

Activity of 2-amino-3-chloro-1,4-naphthoquinones of Formula I against *P. falciparum*.

| —NR₂ | Strain | $IC_{50}$ (ng/mL) | $IC_{90}$ (ng/mL) |
|---|---|---|---|
| —NH₂ | $W_2$ | 37.3 | 83.4 |
| | $D_2$ | 192.0 | 355.9 |
| —N(morpholino) | $W_2$ | 8884.5 | 49662.1 |
| | $D_6$ | 32008.7 | 40505.1 |
| —N(pyrrolidino) | $W_2$ | 2522.1 | 11375.7 |
| | $D_6$ | 9601.2 | 14184.2 |
| —NHC₆H₅ | $W_2$ | 11869.5 | 23029.4 |
| | $D_6$ | 15929.6 | 19182.8 |
| chloroquine* | $W_2$ | 72 | — |
| | $D_6$ | 3 | — |
| mefloquine* | $W_2$ | 1 | — |
| | $D_6$ | 9 | — |
| pyrimethamine* | $W_2$ | 68 | — |
| | $D_6$ | 1 | — |
| sulfadoxine* | $W_2$ | 13353 | — |
| | $D_6$ | 2784 | — |

*Non-quinoid compounds included for comparison purposes

Substituted 2-amino-3-chloro-1,4-naphthoquinones were found to be somewhat effective antimalarial agents, and found to be less effective antimalarial agents than the unsubstituted compound. 2-pyrrolidino-3-chloro-1,4-naphthoquinone was found to have an $IC_{50}$ against the $W_2$ strain of *P. falciparum* of 2522.1 ng/mL, and an $IC_{90}$ of 11375.7 ng/mL. This compound also has an $IC_{50}$ against the $D_6$ strain of 9601.2 ng/mL, and an $IC_{90}$ of 14184.2 ng/mL. This would seem to indicate that, as seen in Table 1, 2-pyrrolidino-3-chloro-1,4-naphthoquinone is comparable in antimalarial activity to sulfadoxine. However, this compound is less effective than chloroquine or pyrimethamine against *P. falciparum*. 2-morpholino-3-chloro-1,4-naphthoquinone and 2-anilino-3-chloro-1,4-naphthoquinone were also tested as antimalarial agents. The results, listed in Table 1, would seem to indicate that these compounds are significantly less effective than 2-pyrrolidino-3-chloro-1,4-naphthoquinone as antimalarial agents. It is possible that placing substituent groups on the amino group reduces the basicity or stearic accessibility of the amino group, turning it into a less effective binding site and hindering its ability to interact with enzymes in *P. falciparum*.

Figure 2:
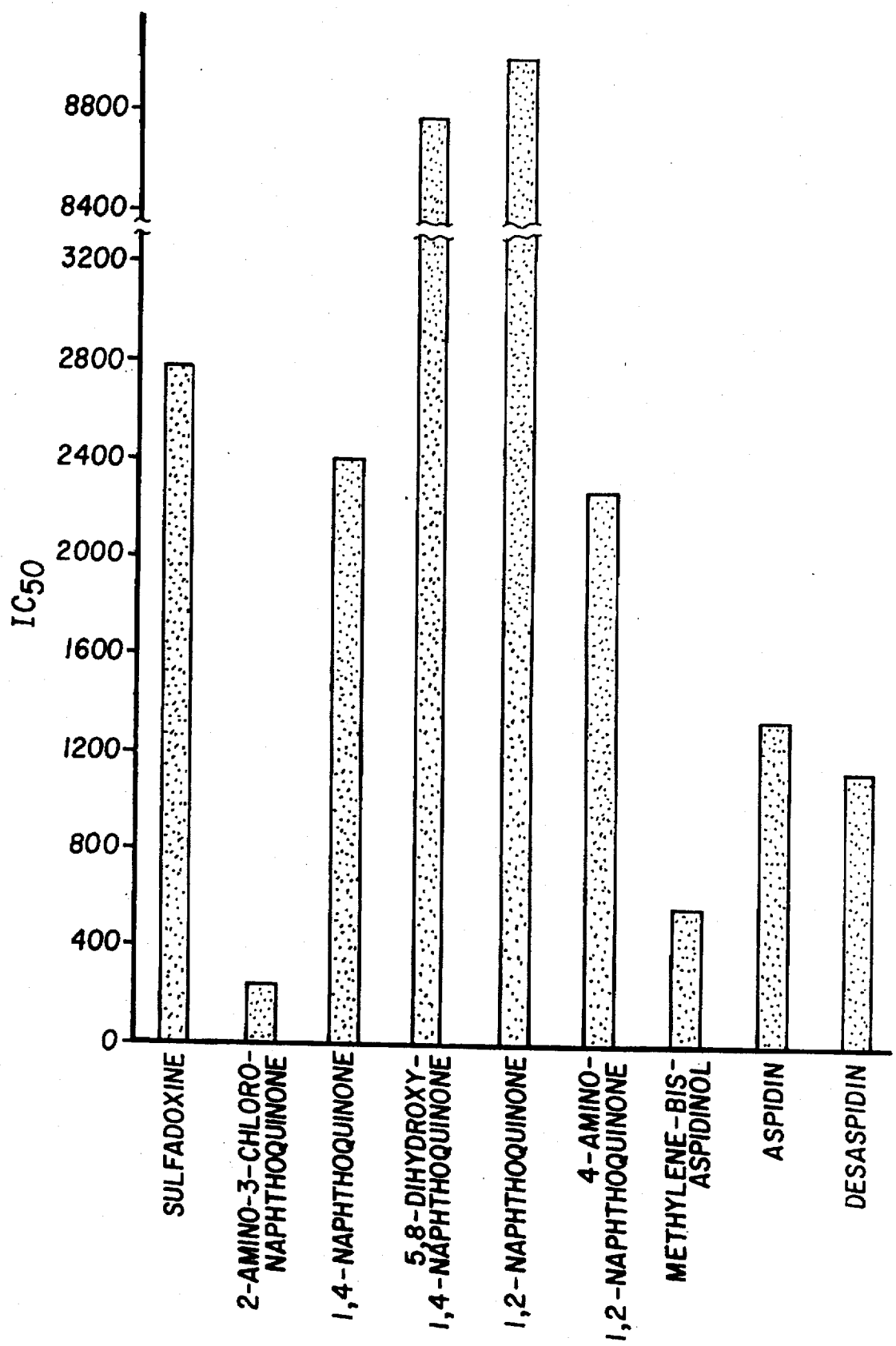
FIG. 2 compares the antiplasmodial activity of selected naphthoquinones and aspidinol derivatives toward the $D_6$ strain of *P. falciparum* to that of sulfadoxine.

In view of the efficacy of certain 2-hydroxy-1,4-naphthoquinones against *P. falciparum*, as well as the known antimalarial activity of polyhydroxy-1,4-naphthoquinones, a series of hydroxylated naphthoquinones was tested for antimalarial activity. 1,4-Naphthoquinone was itself tested as well, allowing us to study the effect of a hydroxyl group on naphthoquinone antimalarial activity. The results are tabulated in Table 2. 1,4-Naphthoquinone was found to exhibit significant antimalarial activity; in fact, as shown in FIG. 2, the activity of 1,4-naphthoquinone against the $D_6$ strain of *P. falciparum* was found to be greater than that of the known antimalarial compound sulfadoxine ($IC_{50}$ for 1,4-naphthoquinone=2393 ng/mL; $IC_{50}$ for sulfadoxine=2784 ng/mL). Also, as shown in FIG. 1, the sulfadoxine-resistant $W_2$ strain is vastly more vulnerable to 1,4-naphthoquinone than it is to sulfadoxine. Hydroxylation of 1,4-naphthoquinone in the 2-position leads to a tenfold decrease in antimalarial activity. Placement of a small alkyl group such as methyl in the 3-position leads to a still further decrease in activity; however, as the size of the hydrocarbon substituent increases, antimalarial activity appears to increase significantly. These results, shown in Table 2, appear to be consistent with the work on 2-alkyl-3-hydroxy-1,4-naphthoquinone antimalarial compounds described by Feiser et al. (J. Amer. Chem. Soc., vol. 70, page 3156 [1948].).

TABLE 2

Activity of 1,4-naphthoquinone and hydroxylated derivatives against *P. falciparum*.

| Compound | Strain | $IC_{50}$ (ng/mL) | $IC_{90}$ (ng/mL) |
|---|---|---|---|
| 1,4-naphthoquinone | $W_2$ | 1292.0 | 1696.6 |
|  | $D_6$ | 2393.3 | 3225.0 |
| 2-hydroxy-1,4-naphthoquinone | $W_2$ | 11658.7 | 15539.8 |
|  | $D_6$ | 19396.0 | 26688.0 |
| 2-hydroxy-3-methyl-1,4-naphthoquinone | $W_2$ | 22587.6 | 31445.6 |
|  | $D_6$ |  | ineffective |
| 2-hydroxy-3-(3-methyl-2-butenyl)-1,4-naphthoquinone | $W_2$ | 10193.3 | 31390.5 |
|  | $D_6$ | 8327.4 | 11440.6 |
| 5-hydroxy-1,4-naphthoquinone | $W_2$ | 12690.5 | 22293.6 |
|  | $D_6$ | 26568.0 | 35010.3 |
| 5,8-dihydroxy-1,4-naphthoquinone | $W_2$ | 2531.1 | 3547.6 |
|  | $D_6$ | 8738.2 | 10460.0 |
| chloroquine | $W_2$ | 72 | — |
|  | $D_6$ | 3 | — |
| mefloquine | $W_2$ | 1 | — |
|  | $D_6$ | 9 | — |
| pyrimethamine | $W_2$ | 68 | — |
|  | $D_6$ | 1 | — |
| sulfadoxine | $W_2$ | 13353 | — |
|  | $D_6$ | 2784 | — |

This work was then extended to other hydroxylated naphthoquinones, specifically 5-hydroxy-1,4-naphthoquinone and 5,8-dihydroxy-1,4-naphthoquinone. As reported in Table 2, it was found that monohydroxylation of 1,4-naphthoquinone in the 5-position leads to a significant decrease in antimalarial activity. In fact, the antimalarial activity of 5-hydroxy-1,4-naphthoquinone appears to be lower than that of 2-hydroxy-1,4-naphthoquinone. The efficacy of 5,8-dihydroxy-1,4-naphthoquinone against *P. falciparum* was then tested, and compared to that of 5-hydroxy-1,4-naphthoquinone. The dihydroxy compound was found to be about five times as effective against the $W_2$ strain of *P. falciparum* as the monohydroxy compound ($IC_{50}$ for 5,8-dihydroxy-1,4-naphthoquinone=2531 ng/mL; $IC_{50}$ for 5-hydroxy-1,4-naphthoquinone=12691 ng/mL), and three times as effective against the $D_6$ strain as the monohydroxy compound ($IC_{50}$ for 5,8-dihydroxy-1,4-naphthoquinone= 8738 ng/mL; $IC_{50}$ for 5-hydroxy-1,4-naphthoquinone= 26568 ng/mL). While 5,8-dihydroxy-1,4-naphthoquinone is significantly less effective against malaria than sulfadoxine in $D_6$ *P. falciparum*, there is reason to believe that 5,8-dihydroxy-1,4-naphthoquinone may be an effective drug for use against sulfadoxine-resistant bacteria. This conclusion is drawn because 5,8-dihydroxy-1,4-naphthoquinone was found to be more than five times as effective against the sulfadoxine-resistant $W_2$ strain of *P. falciparum* as sulfadoxine itself ($IC_{50}$ for 5,8-dihydroxy-1,4-naphthoquinone= 2531 ng/mL; $IC_{50}$ for sulfadoxine=13353 ng/mL), as shown in FIG. 1. However, as shown in FIG. 2, 5,8-dihydroxy-1,4-naphthoquinone is less effective than sulfadoxine against $D_6$ *P. falciparum*.

While many 2-hydroxy-1,4-naphthoquinones are well-known antimalarial agents, little or no work on the efficacy of the closely related 1,2-naphthoquinones as antimalarial agents has been done. Such research would seem to be of interest since 2-hydroxy-1,4-naphthoquinone probably exists in equilibrium with an isomeric 1,2-naphthoquinone, as shown in equation (1):

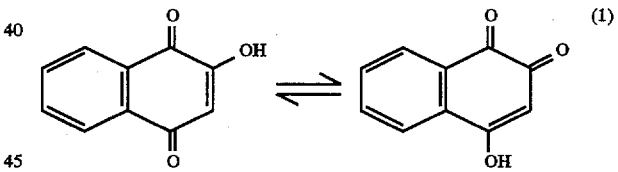

(1)

In an effort to fill this gap, several 1,2-naphthoquinones were tested for antiplasmodial activity against *P. falciparum*. 1,2-naphthoquinone was found to show significant antimalarial activity, as reported in Table 3. In fact, it was found to be very nearly as effective as 1,4-naphthoquinone against the sulfadoxine-resistant $W_2$ strain of *P. falciparum* ($IC_{50}$ for 1,2-naphthoquinone=1510 ng/mL; $IC_{50}$ for 1,4-naphthoquinone=1292 ng/mL). These naphthoquinones are therefore on the order of ten times as effective against sulfadoxine-resistant *P. falciparum* as sulfadoxine itself (see FIG. 1), making both 1,4-naphthoquinone and 1,2-naphthoquinone potentially useful against drug-resistant microorganisms. However, as shown in FIG. 2, 1,2-naphthoquinone was found to be significantly less effective than 1,4-naphthoquinone against the $D_6$ strain of *P. falciparum* ($IC_{50}$ for 1,2-naphthoquinone=8995 ng/mL; $IC_{50}$ for 1,4-naphthoquinone=2393 ng/mL). Although the reasons for this difference are not clearly understood, it is possible that 1,2-naphthoquinone may be a less effective antiplasmodial agent than 1,4-naphthoquinone.

TABLE 3

Activity of 1,2-naphthoquinones against *P. faiciparum*.

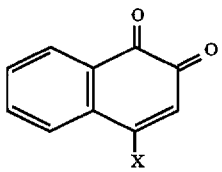

| −X | Strain | IC$_{50}$ (ng/mL) | IC$_{90}$ (ng/mL) |
|---|---|---|---|
| −H | W$_2$ | 1510.0 | 3651.1 |
| | D$_6$ | 8995.2 | 12465.4 |
| −NH$_2$ | W$_2$ | 566.5 | 1961.3 |
| | D$_2$ | 2262.9 | 2870.9 |
| −SO$_3$K | W$_2$ | 1671.3 | 8224.4 |
| | D$_6$ | 7753.2 | 12117.7 |
| | W$_2$ | 2522.1 | 11375.7 |
| chloroquine* | W$_2$ | 72 | — |
| | D$_6$ | 3 | — |
| mefloquine* | W$_2$ | 1 | — |
| | D$_6$ | 9 | — |
| pyrimethamine* | W$_2$ | 68 | — |
| | D$_6$ | 1 | — |
| sulfadoxine* | W$_2$ | 13353 | |
| | D$_6$ | 2784 | — |

*Non-quinonoid compounds included for comparison purposes 1,2-naphthoquinones having substituents in the 4-position were also tested. 4-Amino-1,2-naphthoquinone was tested as an antimalarial agent, and found to be significantly more active against *P. falciparum* than 1,2-naphthoquinone. This increase in activity was seen against both the W$_2$ and the D$_6$ strains (see FIG. 1 and FIG. 2, respectively). In fact, 4-amino-1,2-naphthoquinone appears to be more effective against the sulfadoxine-vulnerable D$_6$ strain of *P. falciparum* than sulfadoxine itself (IC$_{50}$ for 4-amino-1,2-naphthoquinone=2263 ng/mL; IC$_{50}$ for sulfadoxine=2784 ng/mL). The potassium salt of 1,2-naphthoquinone-4-sulfonic acid was also tested, and found to exhibit fairly strong activity against the W$_2$ strain of *P. falciparum* (IC$_{50}$= 1671 ng/mL), and significantly weaker activity against the D6 strain (IC$_{50}$=7753 ng/mL). These results are very similar to those obtained for 1,2-naphthoquinone, and suggest that 1,2-naphthoquinone-4-sulfonic acid salts may be useful against sulfadoxine-resistant strains of *P. falciparum*.

Thus, it appears that the naphthoquinones described herein may have antimalarial activity. Several, including 2-amino-3-chloro-1,4-naphthoquinone, 1,4-naphthoquinone, and 4-amino-1,2-naphthoquinone, appear to be more effective than sulfadoxine against both the W$_2$ and D$_6$ strains of *P. falciparum*. These compounds are of therefore of great interest as possible antimalarial agents. Other compounds, including 2-pyrrolidino-3-chloro-1,4-naphthoquinone, 1,4-naphthoquinone, 5,8-dihydroxy-1,4-naphthoquinone, 1,2-naphthoquinone, and potassium 1,2-naphthoquinone-4-sulfonate, were found to be significantly less active than sulfadoxine against the D$_6$ strain of *P. falciparum*. However, they were also found to be quite effective against the sulfadoxine-resistant W$_2$ strain of *P. falciparum*. It is, therefore, hoped that these compounds, or closely related compounds, may have therapeutic utility in combatting infection by drug-resistant *P. falciparum* strains.

II. Aspidinol Derivatives

As previously described, methylene-bis-2,4-dihydroxybenzene and methylene-bis-2,6-dihydroxybenzene derivatives were found to possess antimicrobial activity. The human parasite *P. falciparum* was exposed to solutions of a series of compounds of this type in an effort to determine whether they exhibit significant antimalarial activity. The procedure used in this study was identical to that used for the naphthoquinone compounds.

The compounds chosen for study were structurally related to the drug aspidinol (1-[2,6-dihydroxy-4-methoxy-3-methylphenyl]-1-butanone; formula V).

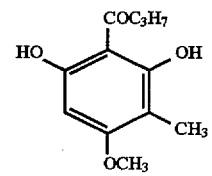

The selected compounds included:

methylene-bis-aspidinol (methylene-bis-[2,4-dihydroxy-6-methoxy-5-methyl-3-butyrylbenzene]; formula VI);

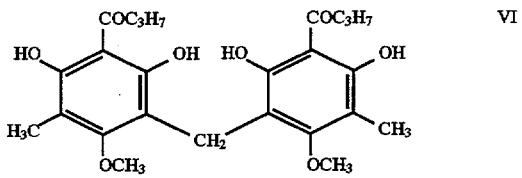

desaspidin (2-[[2,4-dihydroxy-6-methoxy-3-butyrylphenyl]methyl]-3,5-dihydroxy-4,4-dimethyl-6-butyryl-2,5-cyclohexadien-1-one; formula VII );

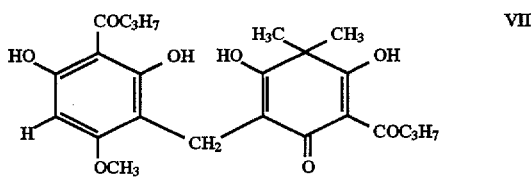

aspidin (2-[[2,6-dihydroxy-4-methoxy-3-methyl-5-butyrylphenyl]methyl]-3,5-dihydroxy-4,4-dimethyl-6-butyryl-2,5-cyclohexadien-1-one; formula VIII);

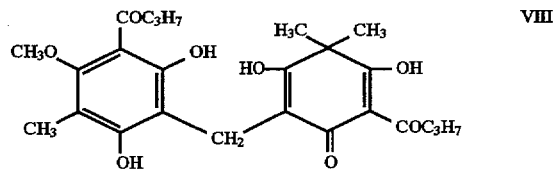

flavaspidic acid (2-[[2,4,6-trihydroxy-3-methyl-5-butyrylphenyl]methyl]-3,5-dihydroxy-4,4-dimethyl-6-butyryl-2,5-cyclohexadien-1-one; formula IX); and

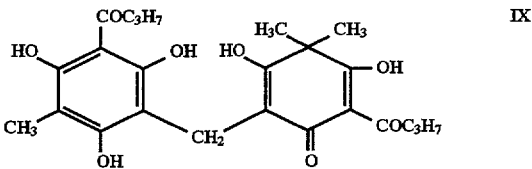

albaspidin (methylene-bis-[3,5-dihydroxy-4,4-dimethyl-6-butyryl-2,5-cyclohexadien-1-one]; formula X).

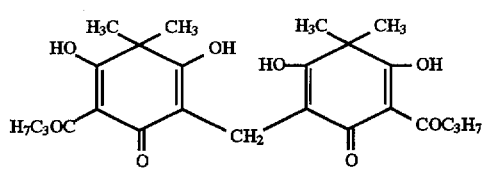

When these compounds were tested for antimalarial activity against *P. falciparum*, several were found to show significant activity, as reported in Table 4. Methylene-bis-aspidinol, in particular, was found to show very high activity against both the $D_6$ strain ($IC_{50}$=325 ng/mL) and the $W_2$ strain ($IC_{50}$=574 ng/mL).

of sulfadoxine. This would seem to indicate that methylene-bis-aspidinol may have therapeutic utility as an antimalarial agent.

Desaspidin and aspidin were also tested for antimalarial activity. As shown in FIGS. 1 and 2, these compounds did show significantly lower activity against both the $W_2$ and $D_6$ strains of *P. falciparum* than methylene-bis-aspidinol. However, they were still 2 to 2½ times as active against the $D_6$ strain as sulfadoxine. Thus, desaspidin and aspidin, like methylene-bis-aspidinol, may be therapeutically useful alternatives to sulfadoxine.

However, when flavaspidic acid and albaspidin were tested, their activity against *P. falciparum* was found to be so low that they are, for practical purposes, ineffective as antimalarial agents (Table 4). Some interesting conclusions can be drawn from these results. First, the presence of a substituted dihydroxyphenyl group would appear to be important to the bioactivity of these compounds. Replace-

TABLE 4

Activity of aspidinol derivatives against *P. falciparum*.

| Compound | Strain | $IC_{50}$ (ng/mL) | $IC_{90}$ (ng/mL) |
|---|---|---|---|
| [structure] | $W_2$ | 325.2 | 443.4 |
|  | $W_6$ | 573.5 | 780.7 |
| [structure] | $W_2$ | 956.5 | 1259.5 |
|  | $D_6$ | 1136.9 | 1561.5 |
| [structure] | $W_2$ | 1079.8 | 1444.3 |
|  | $D_6$ | 1347.9 | 1763.2 |
| [structure] | $W_2$ | 13886.4 | 21844.4 |
|  | $D_6$ | 11882.5 | 23924.7 |
| [structure] | $W_2$ | inactive |  |
|  | $D_6$ | inactive |  |
| chloroquine | $W_2$ | 72 | — |
|  | $D_6$ | 3 | — |
| mefloquine | $W_2$ | 1 | — |
|  | $D_6$ | 9 | — |
| pyrimethamine | $W_2$ | 68 | — |
|  | $D_6$ | 1 | — |
| sulfadoxine | $W_2$ | 13353 | — |
|  | $D_6$ | 2784 | — |

When the activity of sulfadoxine toward the sulfadoxine-vulnerable $D_6$ strain of *P. falciparum* is compared to that of methylene-bis-aspidinol, it is seen that methylene-bis-aspidinol shows about five times the antiplasmodial activity ment of one of the dihydroxyphenyl groups in methylene-bis-aspidinol with a cyclohexadienone group leads to a measurable decrease in its antimalarial activity. Replacement of both dihydroxyphenyl groups with cyclohexadienone groups effectively destroys antimalarial activity. Second, replacement of a 2,6-dihydroxy-4-methoxyphenyl group with a 2,4,6-trihydroxyphenyl group causes a tenfold decrease in antimalarial activity.

In summary, it appears that methylene-bis-aspidinol, desaspidin, and aspidin show therapeutic potential as effective antimalarial agents.

What is claimed is:

1. A method for killing or inhibiting the growth of the malaria-causing pathogen *Plasmodium falciparum* by exposing the pathogen to an effective amount of a preparation comprising a compound selected from the group consisting of:

a) a compound for formula I:

where —$NR_2$ is $NH_2$ or

—$NR_2$ is —$NH_2$ or —$N(CH_2)_3CH_2$;

b) a compound of formula II;

where each R' is —H or each R' is —OH; and c) a compound of formula III;

where R" is —$NH_2$, —H, or —$SO_3M$, and where M is H, Na or K.

2. A method of claim 1, where the compound is a compound of formula I, where —$NR_2$ is —$NH_2$.

3. A method of claim 2, where the preparation contains the compound of formula I in a concentration of up to 400 ng/mL.

4. A method of claim 1, where the compound is a compound of formula III, where R" is $NH_2$.

5. A method of claim 4, where the preparation contains the compound of formula III in a concentration of up to 3000 ng/mL.

6. A method of claim 1, where the compound is a compound of formula I, where —$NR_2$ is

—$N(CH_2)_3CH_2$.

7. A method of claim 1, where the compound is a compound for formula II, where each R' is —H.

8. A method of claim 1, where the compound is a compound of formula II, where each R' is —OH.

9. A method of claim 1, where the compound is a compound of formula III, where R" is —H.

10. A method of claim 1, where the compound is a compound of formula III, where R" is —$SO_3M$.

* * * * *